United States Patent
Kojima et al.

(10) Patent No.: US 9,552,659 B2
(45) Date of Patent: Jan. 24, 2017

(54) X-RAY CT DEVICE, AND IMAGE RECONFIGURATION METHOD

(71) Applicant: HITACHI MEDICAL CORPORATION, Tokyo (JP)

(72) Inventors: Shinichi Kojima, Tokyo (JP); Keisuke Yamakawa, Tokyo (JP); Fumito Watanabe, Tokyo (JP); Yushi Tsubota, Tokyo (JP); Yasutaka Konno, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 32 days.

(21) Appl. No.: 14/655,589

(22) PCT Filed: Jan. 15, 2014

(86) PCT No.: PCT/JP2014/050586
§ 371 (c)(1),
(2) Date: Jun. 25, 2015

(87) PCT Pub. No.: WO2014/115625
PCT Pub. Date: Jul. 31, 2014

(65) Prior Publication Data
US 2015/0325012 A1    Nov. 12, 2015

(30) Foreign Application Priority Data
Jan. 28, 2013    (JP) ................................ 2013-013161

(51) Int. Cl.
*G06K 9/00* (2006.01)
*G06T 11/00* (2006.01)
(Continued)

(52) U.S. Cl.
CPC ............. *G06T 11/005* (2013.01); *A61B 6/032* (2013.01); *A61B 6/4021* (2013.01);
(Continued)

(58) Field of Classification Search
None
See application file for complete search history.

(56) References Cited

U.S. PATENT DOCUMENTS

| 6,169,779 | B1 * | 1/2001 | Lai .......................... | A61B 6/032 378/15 |
| 2009/0168952 | A1 * | 7/2009 | Mori ....................... | A61B 6/032 378/15 |

(Continued)

FOREIGN PATENT DOCUMENTS

WO    2011/018729 A1    2/2011

OTHER PUBLICATIONS

International Preliminary Report on Patentability received in corresponding International Application No. PCT/JP2014/050586 dated Aug. 6, 2015.

(Continued)

*Primary Examiner* — Tahmina Ansari
(74) *Attorney, Agent, or Firm* — Mattingly & Malur, PC

(57) ABSTRACT

Difference of resolution depending on imaging position in one reconstructed image generated in the FFS method is reduced to improve measurement accuracy. The X-ray CT device interpolates missing data of the projection data obtained by the FFS method with view direction interpolation processing using real data of the projection data lining up along the angular direction of the rotational movement, and channel direction interpolation processing using real data of the projection data lining up along the channel direction, and generates a reconstructed image, in which contribution ratios of the projection data having been subjected to the view direction interpolation processing and the projection data having been subjected to the channel direction interpolation processing differ according to position of pixel in the reconstructed image.

20 Claims, 12 Drawing Sheets

(51) Int. Cl.
*G06T 7/00* (2006.01)
*A61B 6/03* (2006.01)
*A61B 6/00* (2006.01)

(52) U.S. Cl.
CPC ............ *A61B 6/5205* (2013.01); *G06T 7/004* (2013.01); *G06T 7/0085* (2013.01); *G06T 11/006* (2013.01); *G06T 2207/10016* (2013.01); *G06T 2207/10081* (2013.01); *G06T 2207/10148* (2013.01); *G06T 2207/30004* (2013.01); *G06T 2211/40* (2013.01)

(56) References Cited

U.S. PATENT DOCUMENTS

| 2010/0034344 | A1* | 2/2010 | Hein | A61B 6/4028 |
| | | | | 378/19 |
| 2011/0176723 | A1* | 7/2011 | Ali | G06T 7/2033 |
| | | | | 382/154 |
| 2013/0343508 | A1* | 12/2013 | Hagiwara | G06T 5/001 |
| | | | | 378/4 |
| 2015/0325012 | A1* | 11/2015 | Kojima | G06T 11/006 |
| | | | | 382/131 |
| 2016/0183900 | A1* | 6/2016 | Fujii | A61B 6/032 |
| | | | | 378/16 |

OTHER PUBLICATIONS

International Search Report of PCT/JP2014/050586.
Ilmar A. Hein et al., Lateral (xy) Direction Balanced Flying Focal Sport helical Cone-Beam CT Algorithm, IEEE Nuclear Science Symposium Conference Record, 2007, pp. 2624-2629.

* cited by examiner

X-RAY CT DEVICE, AND IMAGE RECONFIGURATION METHOD

TECHNICAL FIELD

The present invention relates to an X-ray CT device and an image reconstruction method, especially, a technique for improving spatial resolution to improve accuracy of imaging of a subject.

BACKGROUND ART

Needs for improvement of spatial resolution of X-ray CT (computed tomography) devices are increasing with use of more sophisticated X-ray CT measurement techniques. In order to improve the spatial resolution, use of finer X-ray detectors in the X-ray detection module, i.e., use of X-ray detectors of smaller sizes, is contemplated, but it results in degradation of the S/N ratio of the detected signals.

As a method for improving the spatial resolution without using smaller X-ray detectors in the X-ray detection module, a technique called flying focal spot (FFS) method is disclosed in Patent document 1. The FFS method is a method of producing positional shift of X-ray beam by electromagnetically changing the position of the focal point of X-ray alternately between two positions during the rotational movement of the scanner, and doubling the density of X-ray transmission data by that positional shift.

In the FFS method, the projection data specified by the angular direction of the rotational movement of the scanner (also called view direction or θ direction) and the direction of the channel of the X-ray detection module suffer from missing of data for every view direction associated with the alternate change of the position of the X-ray focal point. In conventional techniques, such missing data are interpolated by using actually measured data (also called real data) obtained for the positions on both sides of the missing data position, for example, for the channel direction or the view direction.

PRIOR ART REFERENCE

Patent Document

Patent document 1: WO2011/018729 A1

SUMMARY OF THE INVENTION

Object to be Achieved by the Invention

According to the FFS method, sampling intervals with a sampling density twice larger than that obtainable in the usual methods can be realized around the rotation center axis of the scanner, but around the X-ray detection part, such double density cannot be obtained, and the sampling intervals are not uniform, either.

Moreover, the magnification degree of the X-ray beam differs according to the distance from the focal point of the X-ray, and a larger magnification degree results in poorer spatial resolution. Therefore, if combination of projection data for counter view angle is taken into consideration, the highest spatial resolution shall be obtained around the imaging center, and the spatial resolution shall be more degraded at a position remoter from the imaging center.

As described above, according to the FFS method, intervals of data sampling points and spatial resolution vary depending on the imaging position. Therefore, the FFS method has a problem that, if the image reconstruction operation is performed by using projection data having been subjected to the conventional interpolation processing, the spatial resolution shall differ for the imaging center part and circumference part in one reconstructed image.

An object of the present invention is to provide a technique for reducing the difference of the spatial resolution depending on the imaging position in one reconstructed image generated by the FFS method, and thereby improving the measurement accuracy.

Means for Achieving the Object

According to the present invention, the aforementioned object is achieved by providing a data interpolation part that interpolates missing data by correcting the imaging position dependency of the data sampling interval and the imaging position dependency of the spatial resolution inherently included in the projection data obtained by the FFS method.

That is, the X-ray CT device of the present invention comprises an X-ray generation part that generates an X-ray, an X-ray detection part that has a plurality of X-ray detectors for detecting the X-ray, detects a transmitted X-ray, and outputs projection data, a rotation part that oppositely disposes the X-ray generation part and the X-ray detection part, and rotationally moves the X-ray generation part and the X-ray detection part, a projection data interpolation part that interpolates the projection data, a reconstruction part that performs a reconstruction operation using the interpolated projection data, and generates a reconstructed image, and a focal point moving part that moves a focal point of the X-ray alternately to a plurality of positions on a rotation orbit plane (orbital plane of rotation) of the rotational movement. The projection data interpolation part interpolates data of data missing positions (referred to as missing data) generated in connection with the movement of the focal point, with a view direction interpolation processing for interpolating the missing data using real data of the projection data lining up along the angular direction of the rotational movement and a channel direction interpolation processing for interpolating the missing data using real data of the projection data lining up along the channel direction, and the reconstruction part generates a reconstructed image in which contribution ratios of the projection data having been subjected to the view direction interpolation processing and the projection data having been subjected to the channel direction interpolation processing are different depending on position of pixel in the reconstructed image.

The movement of the focal point of X-ray includes movement in the circumferential direction of the rotation orbit, and movement in the diametric direction of the rotation orbit.

Effect of the Invention

According to the present invention, there can be provided an X-ray CT device and image reconstruction method with which the imaging position-dependent difference of the resolution in one reconstructed image generated by the FFS method can be reduced, and measurement accuracy can be thereby improved.

MODES FOR CARRYING OUT THE INVENTION

Figure 1:
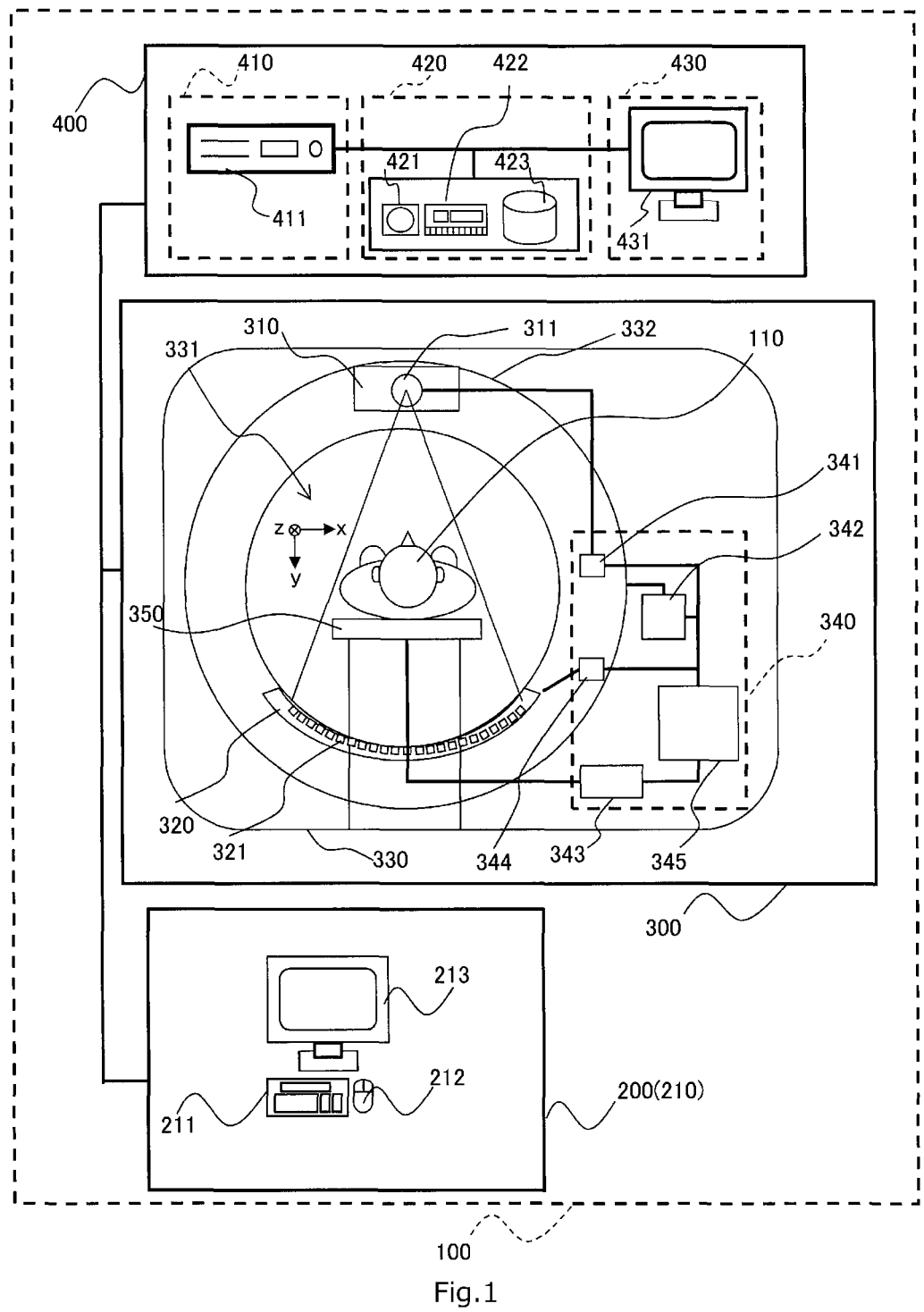
FIG. 1 is an explanatory drawing showing a schematic configuration of an X-ray CT device according to an embodiment of the present invention.

Hereafter, embodiments of the present invention will be explained with reference to the drawings. The same reference numerals are used for the same components in all the appended drawings, and repetition of explanation will be omitted.

The X-ray CT device of an embodiment of the present invention comprises an X-ray generation part that generates an X-ray, an X-ray detection part that has a plurality of X-ray detectors for detecting the X-ray, detects a transmitted X-ray, and outputs projection data, a rotation part that oppositely disposes the X-ray generation part and the X-ray detection part, and rotationally moves the X-ray generation part and the X-ray detection part, a projection data interpolation part that interpolates the projection data, a reconstruction part that performs a reconstruction operation using the interpolated projection data, and generates a reconstructed image, and a focal point moving part that moves a focal point of the X-ray alternately to a plurality of positions on a rotation orbit plane of the rotational movement.

The X-ray detection part is constituted with a plurality of X-ray detectors arranged in the channel direction along the rotational direction, and the projection data include missing of data associated with movement of the focal point. The projection data interpolation part interpolates the data at the data missing positions in the projection data, by a view direction interpolation processing for interpolating the missing data using real data of the projection data lining up along the angular direction of the rotational movement and a channel direction interpolation processing for interpolating the missing data using real data of the projection data lining up along the channel direction, and the reconstruction part generates a reconstructed image in which contribution ratios of the projection data having been subjected to the view direction interpolation processing and the projection data having been subjected to the channel direction interpolation processing are different depending on position of pixel in the reconstructed images.

<Schematic Configuration of X-Ray CT Device>

First, schematic configuration of the X-ray CT device of the embodiment will be explained with reference to FIG. 1. FIG. 1 is an explanatory drawing showing a schematic configuration of the X-ray CT device according to the present invention. The X-ray CT device 100 shown in FIG. 1 comprises an input and output part 200, an imaging part 300, and an image generation part 400.

The input and output part 200 has an input device such as a keyboard 211 and a mouse 212, and an output device including a monitor 213. The monitor 213 has a touch panel function, and may be used as an input device. Since the keyboard 211, mouse 212, and monitor 213 are also used for inputting and setting of imaging conditions, they may also be collectively called an imaging condition input part 210.

The imaging part 300 comprises an X-ray generation part 310, an X-ray detection part 320 that detects X-rays and outputs electric signals indicating intensities of the detected X-rays, a gantry 330 that oppositely carries the X-ray generation part 310 and the X-ray detection part 320, and rotationally moves them, an imaging control part 340 that controls generation and detection of X-rays and operation of rotational movement of the gantry 330, and a table 350 for placing subject.

The image generation part 400 comprises a signal collection part 410, a data processing part 420, and an image display part 430.

The input and output part 200 and the image generation part 400 may not necessarily be provided integrally with the X-ray CT device 100. The functions of them may be realized with, for example, separate devices connected through a network.

The functions of them may also be realized with a device having the functions of both the image generation part 400 and the input and output part 200.

The X-ray generation part 310 of the imaging part 300 has an X-ray tube 311. The X-ray tube 311 has a focal point moving part (not shown in the drawing) for electromagnetically changing the position of the X-ray focal point of the X-ray tube 311 alternately to a plurality of positions locating along the direction of the rotation of the gantry 330. The function of changing the position of the X-ray focal point with this focal point moving part is called FFS function. The focal point moving part can change the position of the X-ray focal point during the rotation of the gantry 330.

The X-ray detection part 320 comprises a plurality of X-ray detection modules 321 constituted by laminating X-ray detectors and photoelectric conversion elements, and which are circularly disposed along the rotation direction of the gantry 330, and disposed along the rotation axis direction of the gantry 330. As for the directions concerning the disposition of the X-ray detection modules 321 in the X-ray detection part 320, the direction along the rotation of the gantry 330 is henceforth referred to as the channel direction, and the direction along the center axis direction of the rotation of the gantry 330 is henceforth referred to as the slice direction. In FIG. 1 and the following drawings, the y-axis is an axis parallel to the center axis of X-ray flux, and the x-axis is an axis perpendicularly intersects with the y-axis in the orbital plane of rotation (mid plain) of the gantry 330. Therefore, it can be said that the x-axis and the y-axis constitute a relative coordinate system within the orbital plane of rotation. The z-axis is an axis parallel to the rotation center axis of the gantry 330, and is an axis perpendicularly intersects with the x-axis and y-axis. As for the relation with the slice direction, the z-axis is parallel to the slice direction.

At the center of the gantry 330, a bore 331 is provided, which is for disposing a subject 110 and a table 350 for placing subject. In the gantry 330, there are provided a rotation plate 332 carrying the X-ray tube 311 and the X-ray detection modules 321, and a driving mechanism (not shown in the drawing) for rotating the rotation plate 332. The table 350 for placing subject has a driving mechanism (not shown in the drawing) for adjusting the position of the subject 110 relative to the gantry 330.

The imaging control part 340 comprises an X-ray controller 341 that controls the positions of the X-ray tube 311 and the X-ray focal point, a gantry controller 342 that controls rotational driving of the rotation plate 332, a table controller 343 that controls driving of the table 350 for placing subject, a detection device controller 344 that controls imaging with the X-ray detection part 321, and a master controller 345 that controls the flow of the operations performed by the X-ray controller 341, the gantry controller 342, the table controller 343, and the detection device controller 344.

<X-Ray Tube, X-Ray Detection Module and Imaging Part>

The distance between the X-ray focal point of the X-ray tube 311 and the X-ray irradiation plane of the X-ray detection module 321 is set to be, for example, 1000 mm. The diameter of the bore 331 of the gantry 330 is set to be, for example, 700 mm.

The X-ray detection module 321 consists of a scintillator and a semiconductor detection device, and detects X-rays. The X-ray detection part 320 is constituted with a plurality of the X-ray detection modules 321 circularly disposed along the rotation direction of the gantry 330 so that they locate at equal distances from a reference position such as average position of the plurality of X-ray focal positions or position of the center of gravity of the X-ray tube 311. The number of the X-ray detection modules 321 included in the X-ray detection part 320 (number of channels) is, for example, 1000. The size of each X-ray detection module 321 for the channel direction is, for example, 1 mm. For ease of the manufacture, it may be configured by preparing a plurality of flat detection devices (detection device modules), and disposing them so that the centers of the planes of the detection devices are circularly disposed to imitate the circular disposition. The time required for rotation of the rotation plate 332 depends on parameters inputted by a user using the imaging condition input part 210. For example, the rotation time is set to be 1.0 second/revolution. The number of times of imaging during one revolution of the imaging part 300 is 900, and whenever the rotation plate 332 rotates 0.4 degree, one time of imaging is performed. The specifications are not limited to these values, and may be variously changed according to the configuration of the X-ray CT device.

<Image Generation Part>

The image generation part 400 comprises a signal collection part 410, a data processing part 420, and an image display part 430. The signal collection part 410 comprises a data acquisition system (DAS, henceforth referred to as "DAS") 411. DAS 411 converts the electric signals (analog signals) outputted by the aforementioned X-ray detection part 321 into digital signals.

The data processing part 420 comprises a central processing unit (CPU) 421, a memory 422, and an HDD (hard disk drive) device 423. In the central processing unit 421 and the memory 422, predetermined programs are loaded and executed to perform various processing such as correction operation of projection data (including the view direction interpolation processing and channel direction interpolation processing described later), and image reconstruction processing. That is, the central processing unit 421, the memory 422, and the predetermined programs cooperate to constitute the projection data interpolation part that performs the interpolation processing of the projection data, and the reconstruction part that performs the reconstruction operation using the projection data to generate a reconstructed image. The HDD device 423 stores data, and performs input and output of data. The image display part 430 is constituted with an image display monitor 431 such as liquid crystal display and CRT (cathode ray tube).

Hereafter, the imaging method using the aforementioned X-ray CT device 100 will be explained. The imaging method mainly comprises three steps of [imaging condition setting step], [imaging step], and [image generation step]. Hereafter, these steps will be explained respectively.

[Imaging Condition Setting Step]

In the imaging condition setting step, the imaging condition input part 210 shown in FIG. 1 displays an input screen on the monitor 213 or another monitor. An operator sets the tube current and tube voltage of the X-ray tube 311, imaging region of the subject 110, resolution power, and so forth by using the mouse 212 and keyboard 211 constituting the imaging condition input part 210, or a touch panel sensor provided on the monitor 213 or the like with looking at the screen. As for the method for moving the position of the focal point of the X-ray tube 311, conditions therefor are determined by an operator according to the resolution desired for the subject 110, and the determined conditions are inputted. If imaging conditions are stored beforehand, they may be read and used. In this case, an operator does not need to input them at every imaging operation.

[Imaging Step]

In the imaging step, when an operator directs the start of the imaging, imaging is performed according to the conditions of the imaging region, tube voltage, and tube current set in the imaging condition setting step already described. A specific example of the method will be explained below. First, the subject 110 is placed on the table 350 for placing subject. The master controller 345 shown in FIG. 1 gives directions to a table controller 343 to move the table 350 for placing subject in a direction perpendicular to the rotation plate 332 (z-axis direction), and stop it when the imaging position of the rotation plate 332 matches the specified imaging position. Disposition of the subject 110 is thereby completed. The master controller 345 also gives a direction at the same timing to the gantry controller 342 to operate a driving motor to start rotation of the rotation plate 332. When the rotation of the rotation plate 332 reaches constant speed, and the disposition of the subject 110 is completed, the master controller 345 gives timing of X-ray irradiation from the X-ray tube 311, and the positions of the X-ray focal point in the FFS imaging (it means that the imaging is performed by the FFS method) to the X-ray controller 341, and gives timings of the imaging in the X-ray detection modules 321 to the detection device controller 344.

As the positions of the X-ray focal point in the FFS imaging, a plurality of positions are set on the orbital plane of rotation of the gantry 330, more precisely, two focal point positions are set along the tangential direction of the orbital plane of rotation, and the focal point is alternately moved to the focal point positions. Although the movement of the focal point of X-ray includes movement in the circumferential direction of the rotation orbit and movement in the diametric direction of the rotation orbit, only the movement in the circumferential direction will be explained in this explanation. Then, imaging is started, that is, irradiation of X-rays and detection of the X-rays by the X-ray detection modules 321 are started. By repeatedly giving directions for such operations as mentioned above, imaging of the whole imaging region is performed. Intensities of the X-rays are converted into electric signals in the X-ray detection modules 321, and sent to DAS 411. In DAS 411, these electric signals are integrated for a certain period of time, and thereby converted into information on X-ray incidence amount per unit time (these are called "projection data"), and then they are stored in the HDD device 423.

When the table 350 for placing subject is repeatedly moved and stopped as described above, one projection data is obtained for every position of the table 350. The imaging may also be performed with moving the table 350 for placing subject along the z-axis direction, as in the known helical scan, not with repeatedly moving and stopping the table 350.

[Image Generation Step]

In the image generation step, a processing for generating an image from the data stored in the HDD device 423 is performed with the central processing unit 421, memory 422, and HDD device 423 provided in the data processing part 420 shown in FIG. 1.

Figure 13:
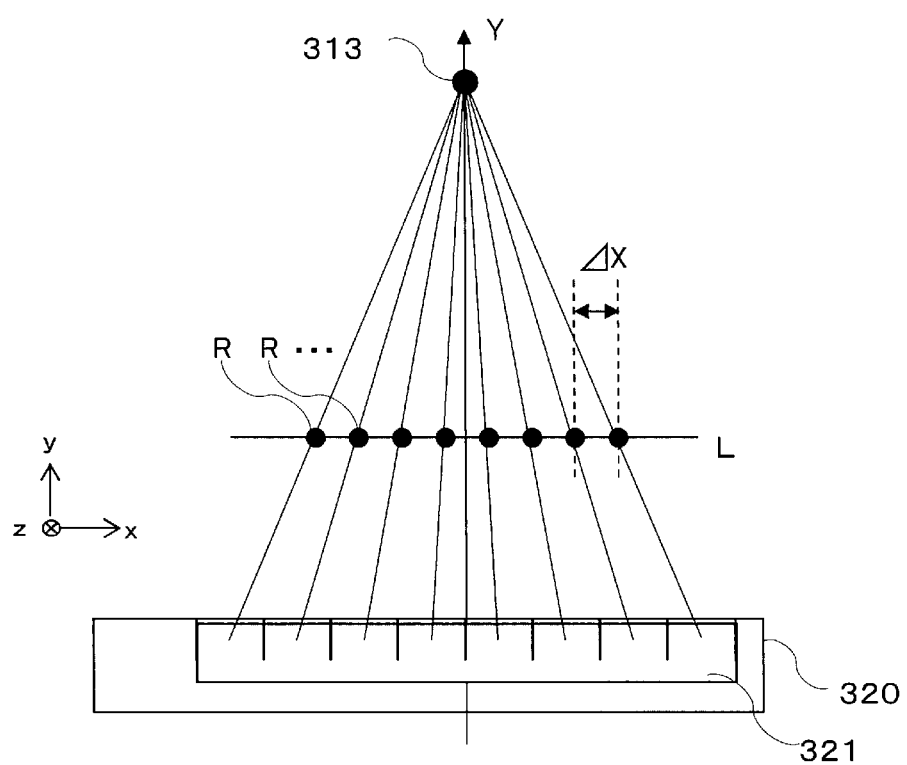
FIG. 13 is an explanatory drawing showing the relative positional relationship of the X-ray focal point 313 and the X-ray detection part 320 used in a usual method.
Figure 14:
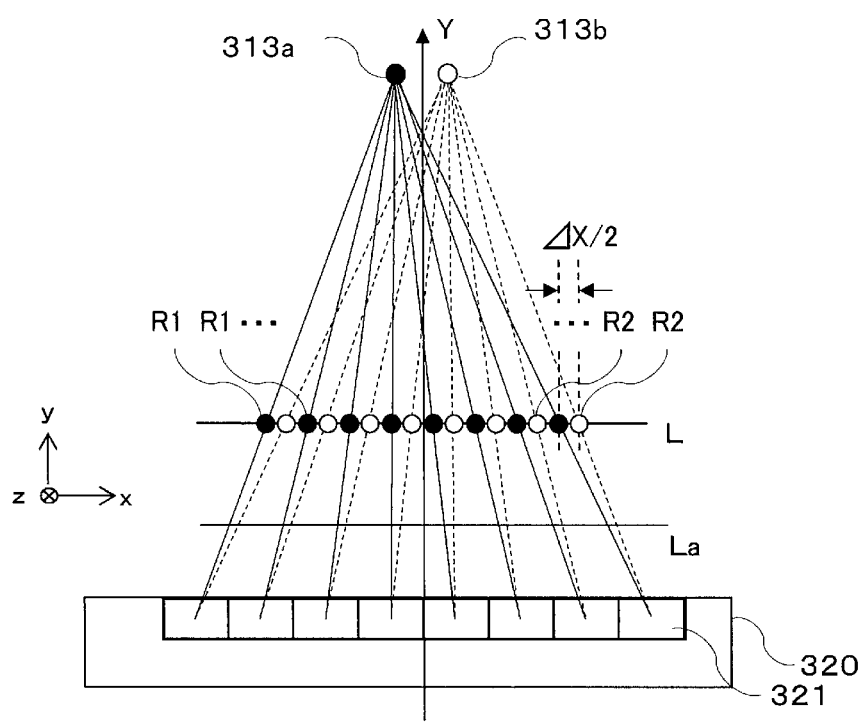
FIG. 14 is an explanatory drawing showing the relative positional relationship of the X-ray focal point 313 and the X-ray detection part 320 used in the FFS method.
Figure 15:
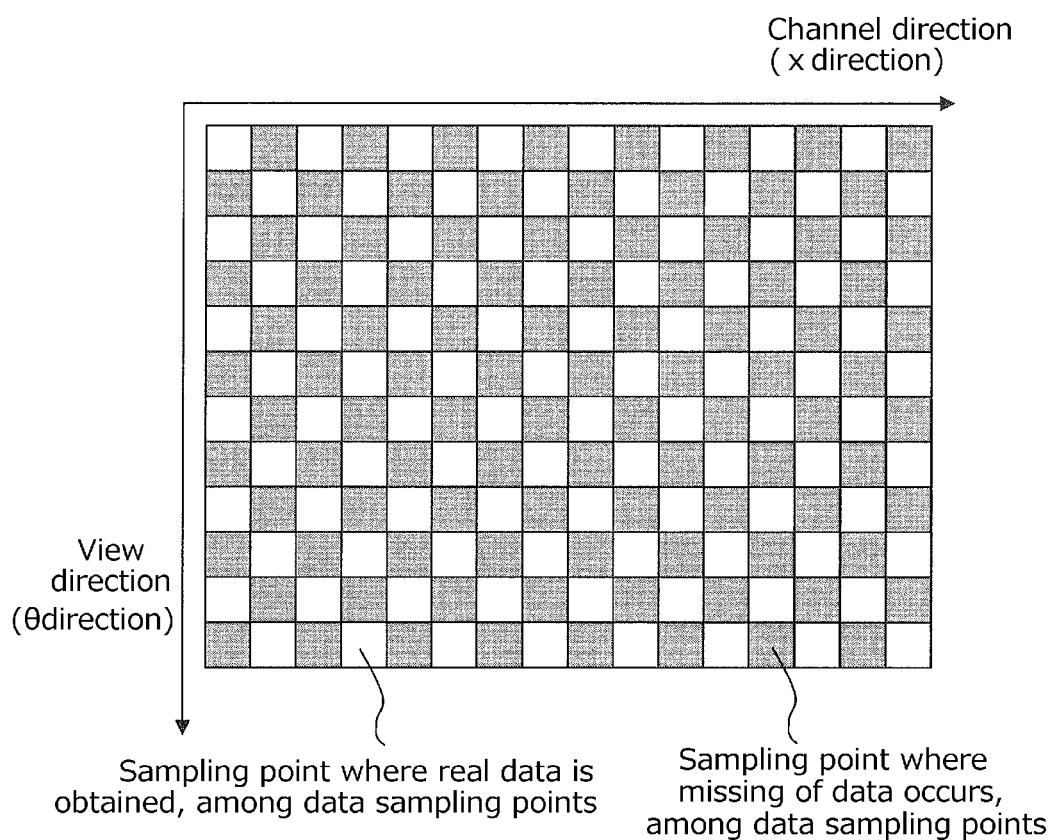
FIG. 15 is an explanatory drawing showing a sinogram obtained by data collection according to the FFS method

In the usual imaging method shown in FIG. 13, the position of the focal point 313 of X-ray is fixed with respect to the X-ray detection module 321. In contrast, in the imaging by the FFS method, the imaging is performed with moving the focal point of X-ray between two positions (313a and 313b), as shown in FIG. 14. In FIGS. 13 and 14, the y-axis is an axis parallel to the center axis of the X-ray flux, and the x-axis is an axis perpendicularly intersecting with the y-axis in the orbital plane of rotation (mid plane). The z-axis is an axis parallel to the rotation center axis of the scanner, and perpendicularly intersects with the x-axis and y-axis. The straight line L is a straight line passing around the rotation center, and parallel to the x-axis. The intersection R of the straight line L and a straight line connecting the X-ray focal point and each X-ray detection module 321 (X-ray beam) corresponds to a data sampling point. In this imaging according to the FFS method, because the X-ray focal point alternately moves with the rotational movement of the scanner, the projection data include missing data along the channel direction and the view direction as shown in FIG. 15.

The present invention is characterized in that, in this [image generation step], the data missed along the channel direction and the view direction in the projection data obtained by imaging of the subject 110 performed by the FFS method (referred to as missing data) are interpolated, and a reconstruction image of the subject 110 is reconstructed by using them.

Figure 2:
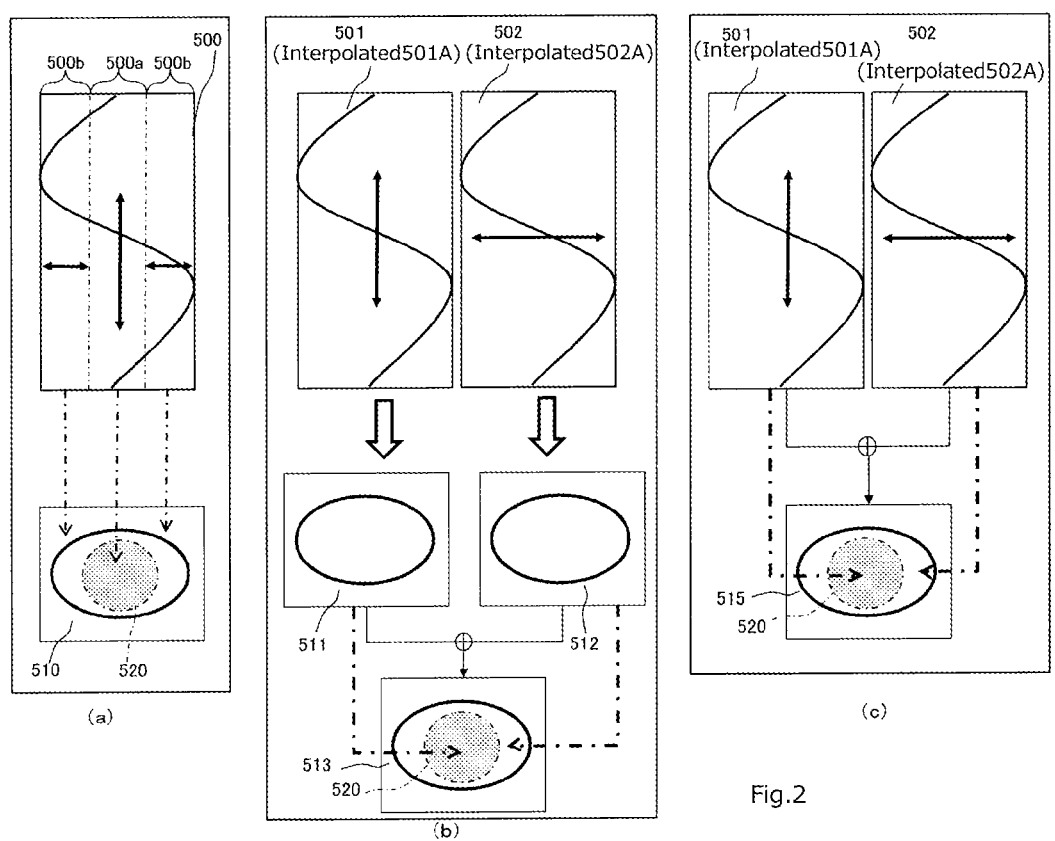
FIG. 2 shows explanatory drawings showing outline of the first embodiment-the third embodiment, wherein (a) shows the first embodiment, (b) shows outline of the second embodiment, and (c) shows outline of the third embodiment.

Embodiments of the method for generating a reconstructed image from projection data of which missing data are interpolated along the channel direction and the view direction are roughly classified into three types of embodiments. Hereafter, outlines of these three types of embodiments will be explained with reference to FIG. 2, and then they will be respectively explained in detail as the first to third embodiments. FIG. 2 includes explanatory drawings showing outlines of the first to third embodiments, in which (a) is an explanatory drawing showing outline of the first embodiment, (b) shows outline of the second embodiment, and (c) shows outline of the third embodiment.

With FIG. 2, an example in which interpolation of missing data is performed along at least one of the view direction and the channel direction using a sinogram of projection data will be explained for convenience of explanation. Sinogram is a graph in which projection data are developed on a coordinate system using a vertical axis that indicates the view direction (also called θ direction) and a horizontal axis that indicates the channel direction (also called x direction). The interpolation processing for the missing data along the view direction and the channel direction may also be performed for the projection data without developing them on a sinogram.

According to the first embodiment, the sinogram is divided into a plurality of regions, and different kinds of interpolation processing are performed depending on the regions. As the interpolation processing, there are used a view direction interpolation processing with which missing data are interpolated by using real data lining up along the view direction, and a channel direction interpolation processing with which missing data are interpolated by using real data lining up along the channel direction.

Specifically, as shown in FIG. 2(a), a sinogram 500 is divided into a region 500a near the center for the channel direction, and regions 500b on both sides of the region 500a (regions relatively nearer to the ends for the channel direction compared with the region 500a), the view direction interpolation processing is performed for the region 500a, and the channel direction interpolation processing is performed for the regions 500b. Then, by using a sinogram 500A obtained after the interpolation processing, the reconstruction operation is performed to generate a reconstructed image 510. In the reconstructed image 510 obtained via such an interpolation processing, contribution ratio of the projection data that have been subjected to the view direction interpolation processing becomes relatively higher in a region around the position corresponding to the rotation center of the gantry 330, and in a region surrounding the foregoing region, contribution ratio of the projection data that have been subjected to the channel direction interpolation processing becomes relatively higher. A circle 520 shown in FIG. 2(a) indicates the boundary of such regions as mentioned above. The same shall apply to FIGS. 2(b) and 2(c). When FOV (also referred to as field of view) is set so that the center of the reconstructed field of view corresponds to the rotation center of the gantry 330, the FOV center, i.e., the image center of the reconstructed image, agrees with the reconstruction point of the rotation center axis in the reconstructed image.

According to the second embodiment, as shown in FIG. 2(b), two of the same projection data are prepared for each position along the slice direction. In FIG. 2(b), the same sinogram 501 and sinogram 502 are used, for example. Then, the view direction interpolation processing is performed for the whole region of one of the sinograms, sinogram 501, to interpolate missing data. The projection data obtained by such an interpolation processing as mentioned above are referred to as "view direction interpolated projection data". Further, the channel direction interpolation processing is performed for the whole region of the other sinogram, sinogram 502, to interpolate missing data. The projection data obtained by such an interpolation processing as mentioned above are referred to as "channel direction interpolated projection data". Then, a view direction interpolated reconstructed image 511 is reconstructed from the view direction interpolated projection data (sinogram 501A). A channel direction interpolated reconstructed image 512 is also reconstructed from the channel direction interpolated projection data (sinogram 502A). Then, the view direction interpolated reconstructed image 511 and the channel direction interpolated reconstructed image 512 of are combined to generate a combined image 513. In the combined image 513, contribution ratio of the view direction interpolated reconstructed image 511 is relatively higher around the imaging center, and the contribution ratio of the channel direction interpolated reconstructed image 512 become relatively higher in a circumferential part with respect to the imaging center.

According to the third embodiment, the view direction interpolated projection data (sinogram 501A) and the channel direction interpolated projection data (sinogram 502A) are also generated as in the second embodiment. Then, convolution operations are performed for the view direction interpolated projection data and the channel direction interpolated projection data, with changing first weight to be multiplied on the view direction interpolated projection data and second weight to be multiplied on the channel direction interpolated projection data according to pixel position on the reconstructed images 515, to generate one reconstructed image 515. Since real coordinates in the reconstructed image 515 are known during the convolution operations, the convolution operations are performed with increasing the first weight relative to the second weight around the imaging center in the reconstructed images 515, and increasing the second weight relative to the first weight in the circumferential part with respect to the imaging center in the reconstructed images 515. Hereafter, the details of the respective embodiments will be explained.

First Embodiment

Figure 3:
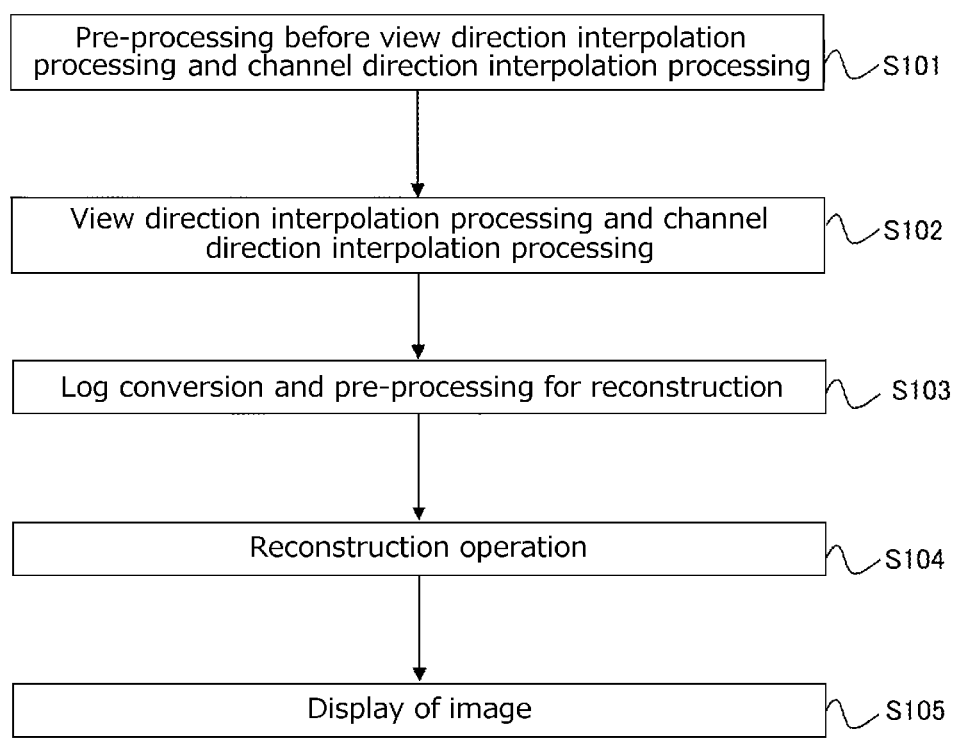
FIG. 3 is a flowchart showing the flow of the processing according to the first embodiment.
Figure 4:
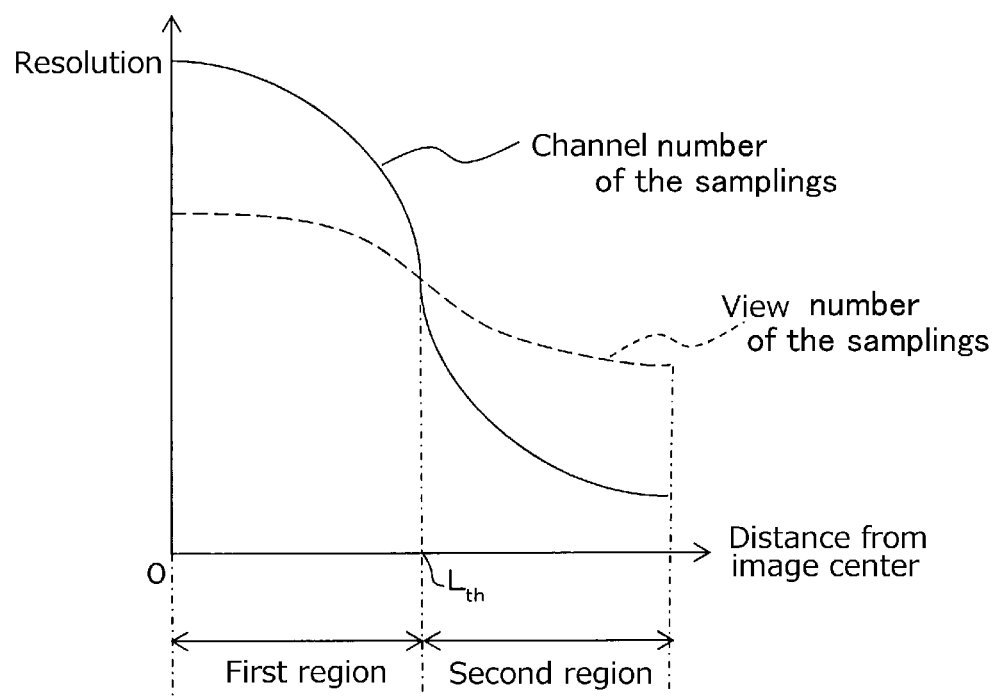
FIG. 4 is an explanatory drawing showing resolution for the view direction and resolution for the channel direction in a reconstructed image.
Figure 5:
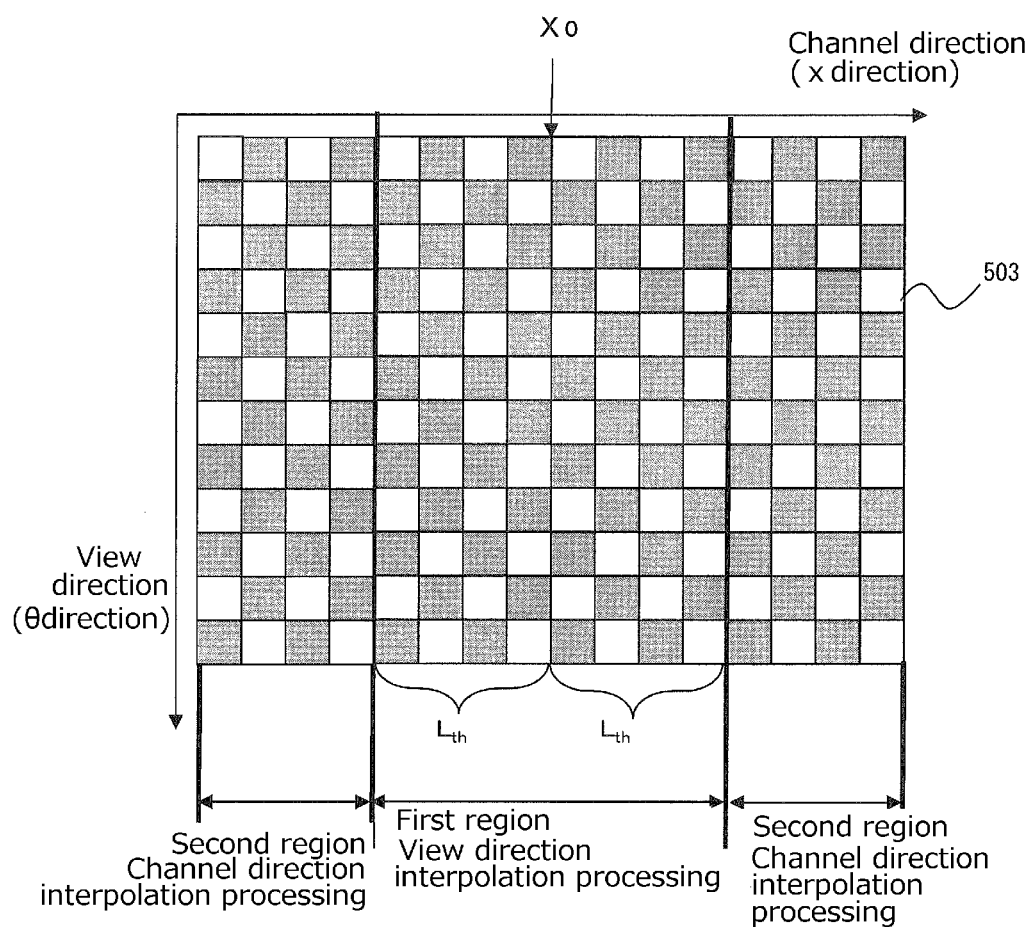
FIG. 5 is an explanatory drawing showing the data interpolation direction on a sinogram in a directionally weighted interpolation processing.
Figure 6:
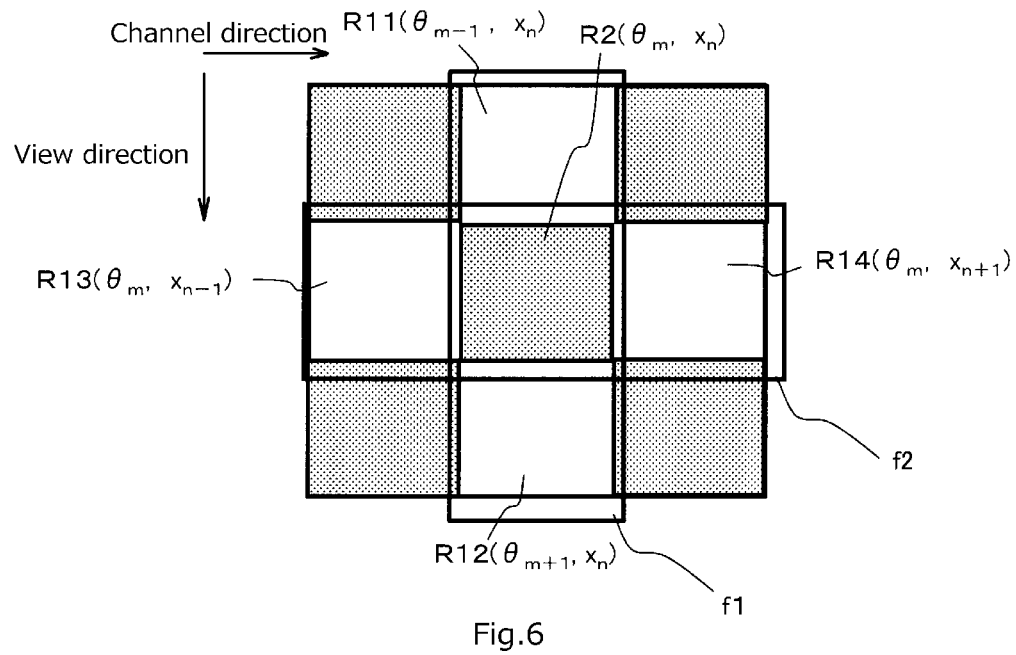
FIG. 6 is an explanatory drawing showing details of the view direction interpolation processing and the channel direction interpolation processing.
Figure 7:
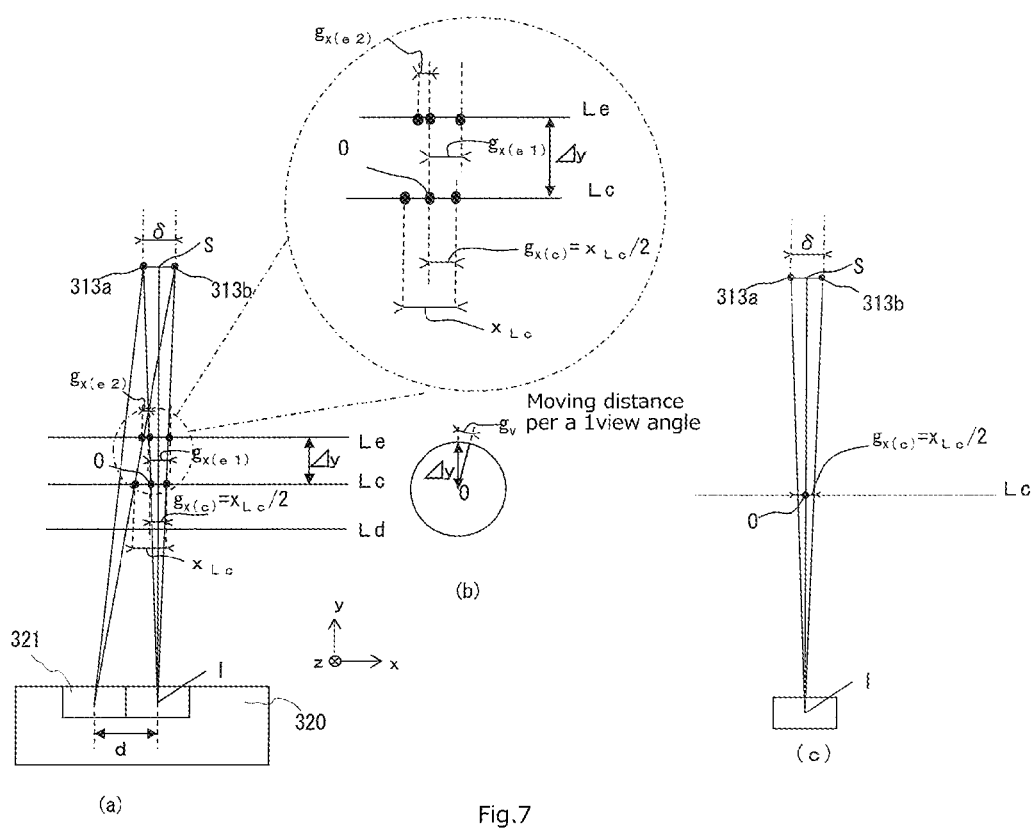
FIG. 7 is an explanatory drawing showing a method for calculating boundary position of view direction interpolation and channel direction interpolation, wherein (a) indicates geometrical relation of X-ray, focal point thereof, and X-ray detector into which the X-ray enters, (b) indicates moving distance corresponding to the rotation angle for one view, and (c) indicates geometrical relation of moving distance of the focal point and data sampling interval at the imaging center.

The first embodiment will be explained with reference to FIG. 2(a) already referred to above, and FIGS. 3 to 7. FIG. 3 is a flowchart showing the flow of the processing of the image generation step of the first embodiment. FIG. 4 is an explanatory drawing showing view number of the samplings and channel number of the samplings in a reconstructed image. FIG. 5 is an explanatory drawing showing the data interpolation directions in the directionally weighted interpolation processing on a sinogram. FIG. 6 is an explanatory drawing showing details of the view direction interpolation processing and the channel direction interpolation processing. FIG. 7 includes explanatory drawings showing a method for calculating boundary position of a view direction interpolation region and a channel direction interpolation region, in which (a) indicates geometrical relation of X-ray, focal point thereof, and X-ray detector into which the X-ray enters, FIG. (b) indicates moving distance corresponding to the rotation angle for one view, and FIG. (c) indicates geometrical relation of moving distance of focal point and data sampling interval at the imaging center. Hereafter, explanations will be made in the order of the steps mentioned in FIG. 3.

(Step S101)

First, the projection data are subjected to a pre-processing required for the view direction interpolation processing and the channel direction interpolation processing (Step S101). As the pre-processing, specifically, correction of linearity of circuit, defect correction (defective pixel correction), or the like is performed, for example. The linearity correction and defect correction are carried out by using known techniques. For the defect correction, for example, the technique described in Japanese Patent Unexamined Publication (Kokai) No. 2005-124613 etc. can be used.

(Step S102)

Then, the projection data obtained by the FFS imaging are subjected to an interpolation processing for missing data (refer to FIG. 2A) (Step S102). As already described, in the FFS imaging, the number of data sampling points for the channel direction increases around the rotation center axis, i.e., the sample density is high, but effective data sampling density for the channel direction becomes lower around the X-ray detection module 321. Therefore, in a reconstructed image reconstructed from the projection data obtained by carrying out the interpolation processing along the channel direction, the spatial resolution (referred to as channel number of the samplings) differs depending on the position of pixel (imaging position). Moreover, since magnification changes depending on the imaging position, also in a reconstructed image reconstructed from the projection data obtained by carrying out the interpolation processing along the view direction, spatial resolution (referred to as the view number of the samplings) differs depending on the position of pixel (imaging position). FIG. 4 is a graph using a coordinate system in which the horizontal axis indicates the distance from the imaging center in a reconstructed image, and the vertical axis indicates the channel number of the samplings and the view number of the samplings. As shown in FIG. 4, the channel number of the samplings is higher than the view number of the samplings near the imaging center, and both the channel number of the samplings and the view number of the samplings more degrade as the position becomes remoter from the imaging center. As for degree of this degradation, degree of the degradation of the channel number of the samplings is larger than that of the view number of the samplings. Therefore, at a certain distance from the imaging center, the view number of the samplings and the channel number of the samplings become equal to each other. This distance is referred to as distance threshold, and represented by $L_{th}$. At a distance larger than the distance threshold $L_{th}$, the view number of the samplings exceeds the channel number of the samplings.

The region of a distance from the imaging center not longer than the distance threshold $L_{th}$ is referred to as "first region", and the region of a distance from the imaging center longer than the distance threshold $L_{th}$ is referred to as "second region". In the first region, the view number of the samplings is relatively low, and the sample density of real data is relatively high for the channel direction. Therefore, the view direction interpolation processing is performed to interpolate missing data. This aims at improvement in the resolution for the view direction. On the other hand, in the second region, although the view number of the samplings is relatively high, the sample density of real data is relatively low in the channel direction. Therefore, the channel direction interpolation processing is performed to interpolate missing data. As a result, the difference of the view number of the samplings and the channel number of the samplings depending on the imaging position in the reconstructed image can be reduced.

Specifically, as shown in FIG. 5, in the sinogram 503 (this is an enlarged drawing of the sinogram 500 shown in FIG. 2A), a region within the distance threshold $L_{th}$ from the position $x_O$ for the channel direction as the center, which position corresponds to the position of the projection data of the rotation center for the channel direction, is defined as the first region, and the view direction interpolation processing is performed for this first region. Further, for the second region defined with a distance from the position $x_O$ for the channel direction longer than the distance threshold $L_{th}$, the channel direction interpolation processing is performed. In the sinogram shown in FIG. 5, the white squares indicate the positions where there are real data, and the gray squares indicate data missing positions.

The view direction interpolation processing and the channel direction interpolation processing will be explained with reference to FIG. 6. The view direction interpolation processing means interpolating missing data at a data missing position by using real data of a position adjacent to the data missing position along the view direction. The channel direction interpolation processing means interpolating missing data at a data missing position by using real data of a position adjacent to the data missing position along the channel direction. For example, in FIG. 6, when data of a data missing position R2 (coordinates ($\theta_m$, $x_n$)) is calculated by using a filter f1 consisting of a matrix of 1×3 including the data missing position R2 at the center, it is calculated by using real data of the data sample point R11 (coordinates ($\theta_{m-1}$, $x_n$)) and the data sample point R12 (coordinates ($\theta_{m+1}$, $x_n$)) adjacent to the data missing position R2 along the view direction. As for the calculation method, calculation result obtained in accordance with, for example, the following equation (1) is used as interpolated data of the data missing position R2.

(Equation 1)

Value of R2={Real data of R11+Real data of R12}/2 (1)

In the channel direction interpolation processing, when data of the data missing position R2 (coordinates ($\theta_m$, $x_n$)) is calculated by using a filter f2 consisting of a matrix of 3×1 including the data missing position R2 at the center, a value calculated by using real data of the data sample point R13 (coordinates ($\theta_m$, $x_{n-1}$)) and the data sample point R14 (coordinates ($\theta_m$, $x_{n+1}$)) adjacent to the data missing position R2 along the channel direction in accordance with, for example, the following equation (2) is used as interpolated data of the data missing position R2.

(Equation 2)

Value of R2={Real data of R13+Real data of R14}/2 (2)

When the data sample point R1 (any one of R11 to R14) is a data missing position, the view direction interpolation and the channel direction interpolation can be similarly performed for it by using real data of the positions on both sides thereof along the view direction or channel direction. The aforementioned sizes of the filters, 1×3 and 3×1, are mere examples, and the size is not limited to these. Further, the value to be interpolated may also be calculated by optionally multiplying a larger weight on real data of a data sample point closer to the data missing position in the filter.

Hereafter, the processing for detecting the boundary of the regions to which the view direction interpolation processing and the channel direction interpolation processing are performed, respectively, i.e., the position corresponding to the distance threshold $L_{th}$ mentioned above, will be explained with reference to FIG. 7. As the premise of the determination of the boundary, it is supposed that the imaging center (reconstruction center point) and the rotation center locate at the same position. The imaging center is represented as O, the midpoint between the X-ray focal point 313a and the X-ray focal point 313b as S, the intersection of the perpendicular line drawn from the midpoint S to the X-ray detection part 320 and the X-ray detection part 320 (more precisely, intersection with the image receiving surface of the X-ray detection module 321) as I, the distance between S and I as SID, and the distance between O and I as OID. Further, the width of the movement of the focal point position is represented as δ, and the number of divided segments along the rotation direction, i.e., the number of views, is represented as V. Furthermore, the straight line passing the imaging center O and parallel to the x-axis is represented as Lc, the sampling interval on the straight line Lc used in usual imaging (imaging is not performed by the FFS method) shown in FIG. 13 is represented as $x_{Lc}$, and the sampling interval on the straight line Lc used in the FFS method is represented as $g_x$. A straight line corresponding to the straight line Lc moved toward the X-ray detection part 320 by Δy is represented as Ld, and a straight line corresponding to the straight line Lc moved toward the X-ray focal point 313a and the X-ray focal point 313b by Δy is represented as Le.

When the best resolution is obtained at the position of the imaging center O in imaging by the FFS method, the sampling interval at the position of the imaging center O on the straight line Lc shown in FIG. 7(a) becomes $x_{Lc}/2$. In this case, from the conditions of similarity of the triangles shown in FIG. 7(c), the following relation is obtained.

[Equation 3]

$$\frac{x_{Lc}/2}{\delta} = \frac{OID}{SID} \qquad (3)$$

As for the straight line Le shifted by Δy from the above position, also from the conditions of similarity, the sampling interval $g_x$ at a position on the straight line Le is represented by the following equation.

[Equation 4]

$$g_x = \delta \times \frac{OID = \Delta y}{SID} \qquad (4)$$

By eliminating δ/SID from the equations (3) and (4), the following relation is obtained,

[Equation 5]

$$g_x = \frac{x_{Lc}}{2} + \frac{x_{Lc}}{2} \frac{\Delta y}{OID} \qquad (5)$$

According to the equation (5), when Δy is positive (Δy is positive on the X-ray focal point side), the value of the sampling interval $g_x$ becomes larger than $x_{Lc}/2$, and thus spatial resolution degrades, whereas, when Δy is negative, the sampling interval becomes smaller than $x_{Lc}/2$, and thus spatial resolution improves. However, the spatial resolution actually degrades even when Δy is negative, as explained below. That is, among two of the sampling intervals or $g_{x(e1)}$ and or $g_{x(e2)}$, which are adjacent to each other on the straight line Le shown in FIG. 7A, $g_{x(e2)}$ is shorter, and or $g_{x(e1)}$ is longer. When Δy is positive, the longer sampling interval is obtained according to the equation (5), and when Δy is negative, the shorter sampling interval is obtained according to the equation (5). When Δy is negative, the longer sampling interval can be obtained from the sum of the longer sampling interval and the shorter sampling interval $g_{x(e2)}$, if the sum is known. If it is assumed that the value of Δy is such a value that the sampling interval is not changed so much for simplification of the explanation, the sum of the longer sampling interval and the shorter sampling interval can be approximated by twice of the sampling interval on the straight line Lc ($=x_{Lc}$), and when Δy is negative, the longer sampling interval gx(e1) can be represented by the following equation.

[Equation 6]

$$g_{x(e1)} = x_{Lc} - \left(\frac{x_{Lc}}{2} + \frac{x_{Lc}}{2}\frac{\Delta y}{OID}\right) = \frac{x_{Lc}}{2} - \frac{x_{Lc}}{2}\frac{\Delta y}{OID}(\Delta y < 0) \quad (6)$$

If this sampling interval is regarded as the sampling interval $g_x$ in the case where Δy is negative, from the equation (5) and the equation (6), where an absolute value is used for Δy, the following relation can be obtained.

[Equation 7]

$$g_x = x_{Lc} - \left(\frac{x_{Lc}}{2} + \frac{x_{Lc}}{2}\frac{\Delta y}{OID}\right) = \frac{x_{Lc}}{2} + \frac{x_{Lc}}{2}\frac{|\Delta y|}{OID} \quad (7)$$

That is, it can be seen that the resolution degrades along the channel direction (x direction) compared with that of the center irrespective of the sign of Δy (positive/negative).

On the other hand, the sampling interval $g_v$ for the view direction corresponds to the distance of the movement of the sampling point by the angle for one view. As shown in FIG. 7(b), when the number of views is sufficiently large, if the circumference of the circle (arc of the circle corresponding to the moving distance) is approximated by a straight line, the moving distance for one view at a position remote by Δy from the imaging center O can be described as the equation (8).

[Equation 8]

$$g_v = \frac{2\pi|\Delta y|}{V} \quad (8)$$

Since the point at which the values of the equations (7) and (8) are the same is the point at which degradation of the resolution for the view direction and degradation of the resolution for the channel direction are the same, circumference of a circle of which radius, i.e., the distance Δy from the center, satisfies the equation (9) is the boundary.

[Equation 9]

$$\frac{x_{Lc}}{2} + \frac{x_{Lc}}{2}\frac{|\Delta y|}{OID} = \frac{2\pi|\Delta y|}{V} \quad (9)$$

The interpolation may be performed for the view direction for the region on the center side of the boundary, and may be performed for the channel direction for the region outside the boundary. The distance Δy from the imaging center O corresponds to the distance threshold $L_{th}$ already mentioned above.

The projection data for the position of the imaging center O is obtained as projection data for the position of the rotation center axis. Therefore, in the first embodiment, for the first region of the projection data of which center is the position of channel of the X-ray detection module 321 intersecting with the perpendicular line drawn from the midpoint position S of the X-ray focal points to the X-ray detection part 320 and passing the imaging center O, which is within the distance threshold $L_{th}$ along the channel direction, missing data are interpolated by performing the view direction interpolation processing, and for the second region remote from the imaging center by a distance longer than the distance threshold $L_{th}$, missing data are interpolated by performing the channel direction interpolation processing. In the aforementioned example, the distance threshold $L_{th}$ is determined by using the values calculated on the basis of the moving distance δ of the focal point of X-ray, the distance SID between the X-ray focal point and the X-ray detection module, and the distance OID between the rotation center and the X-ray detection module. However, in order to measure resolution corresponding to varying distance from the rotation center, it may be determined by using a value calculated on the basis of an image for resolution measurement consisting of an image obtained by imaging of a subject having a known size.

(Step S103)

In Step S103, a pre-processing required for the log conversion or the reconstruction processing is performed (Step S103). This is also performed by using a known technique. The log conversion may also be performed in Step S101 performed before Step S102.

(Step S104)

Using the projection data having been subjected to the pre-processing in Step S103, a reconstruction operation processing is performed to generate a reconstructed image (X-ray CT image) (Step S104). As for the reconstruction algorithm, reconstruction may be performed by using, for example, the FeldKamp method or the sequential approximation method, which are known techniques, and type of the reconstruction algorithm is not particularly limited.

(Step S105)

The X-ray CT image is displayed (Step S105).

According to this embodiment, in the X-ray CT device, difference of the resolution depending on the imaging position in one reconstructed image, which is produced when imaging is performed by the FFS method, can be reduced, and resolution of the reconstructed image can be optimized in accordance with positions of the pixels on the reconstructed image.

In addition, it is expected that the X-ray CT device of the first embodiment shall be further improved by adding horizontal movement of the bed, which is a known technique. Although resolutions at the rotation center of the X-ray CT device and a position remote from the rotation center differ even in a usual X-ray CT image, the degradation of the resolution becomes more marked at a position remote from the rotation center in the FFS method, as previously explained. However, it is expected that resolution shall be improved for a reconstruction field of view desired by a user by making the rotation center and the imaging center (reconstruction center) as closer as possible through horizontal movement and vertical movement of the bed. It can be expected that, in addition to the aforementioned effect, there should be thereby provided improvement in the resolution in a region of interest in a measured X-ray CT image.

In the above explanation, one sinogram is divided into two regions, i.e., the first region and the second region, and either the view direction interpolation processing or the channel direction interpolation processing was performed for each region. However, a connection region including a position corresponding to the distance threshold $L_{th}$ may be provided between the first region and the second region, and the ratio of the view direction interpolation processing and the channel direction interpolation processing to be performed in this connection region may be continuously changed. Furthermore, by defining variables x and θ for the projection data, weight to be multiplied in the view direction interpolation processing and weight to be multiplied in the channel direction interpolation processing may be continuously changed by using a filter function f(x, θ). This is equivalent to using infinite number of sections on the sinogram. Use of a continuously changing filter function makes it possible to suppress generation of discontinuous points or boundaries in an X-ray CT image. As an example of the filter function, a trigonometric function of which value changes with change of the distance from the rotation center of the rotational movement.

Second Embodiment

Figure 8:
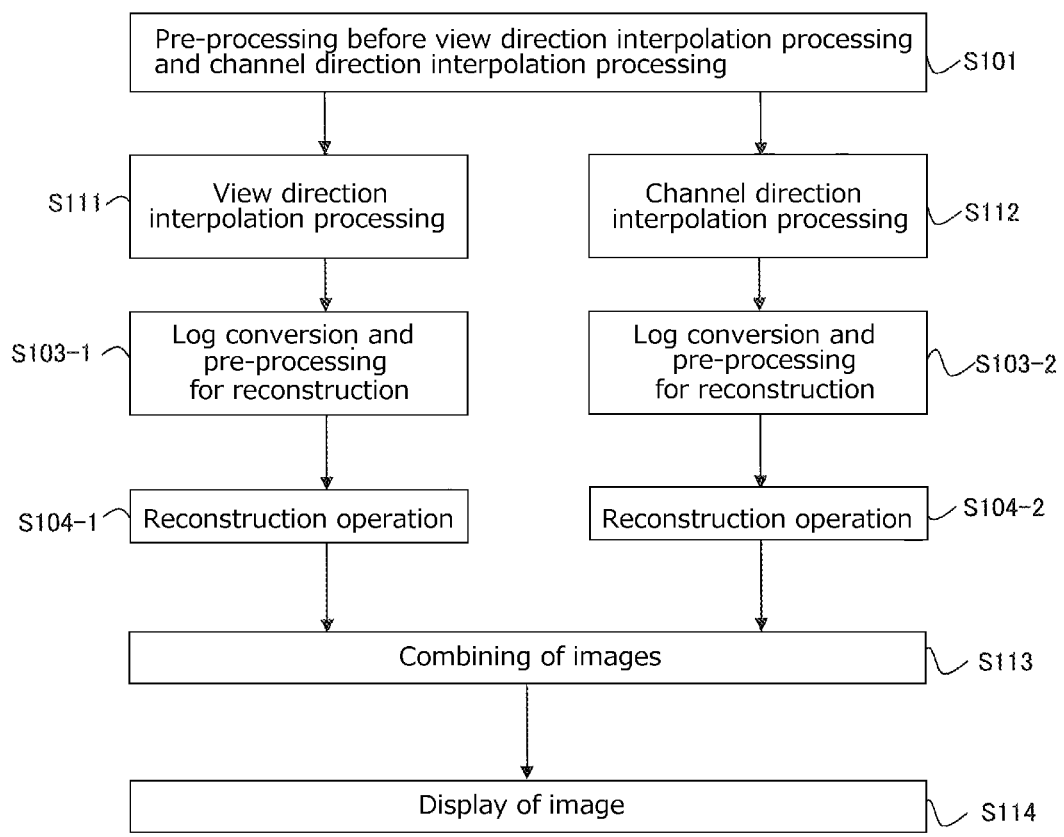
FIG. 8 is a flowchart showing the flow of the processing according to the second embodiment.
Figure 9:
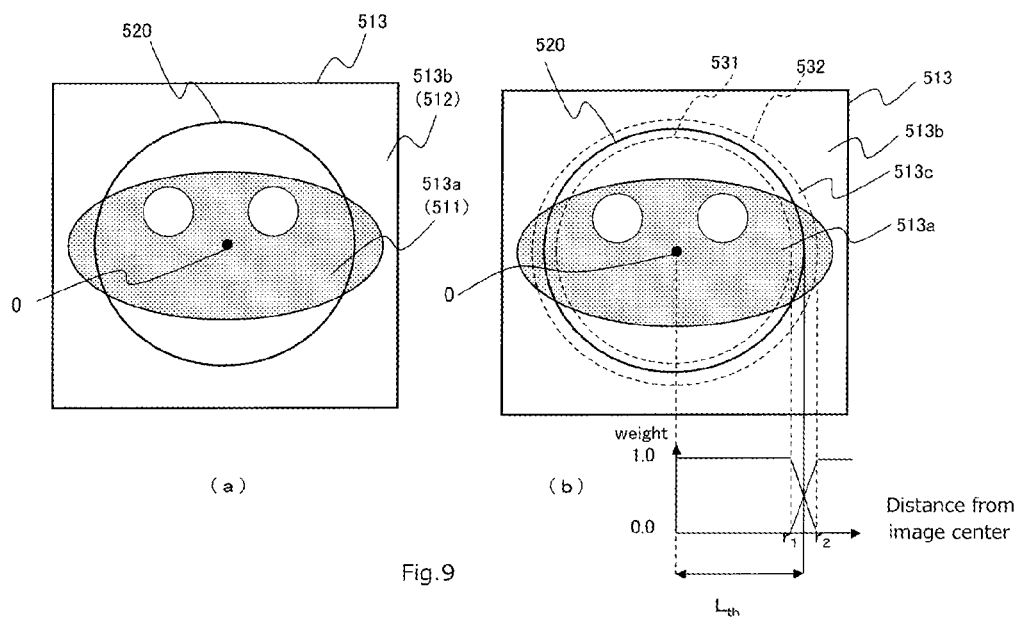
FIG. 9 is an explanatory drawing showing, wherein (a) and (b) shows an example of processing for combining reconstructed images respectively.
Figure 10:
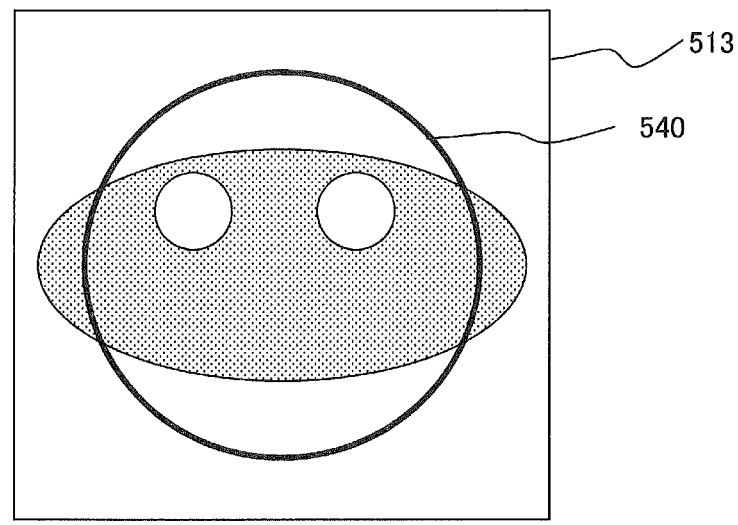
FIG. 10 is an explanatory drawing showing an example of display mode according to the second embodiment.
Figure 11:
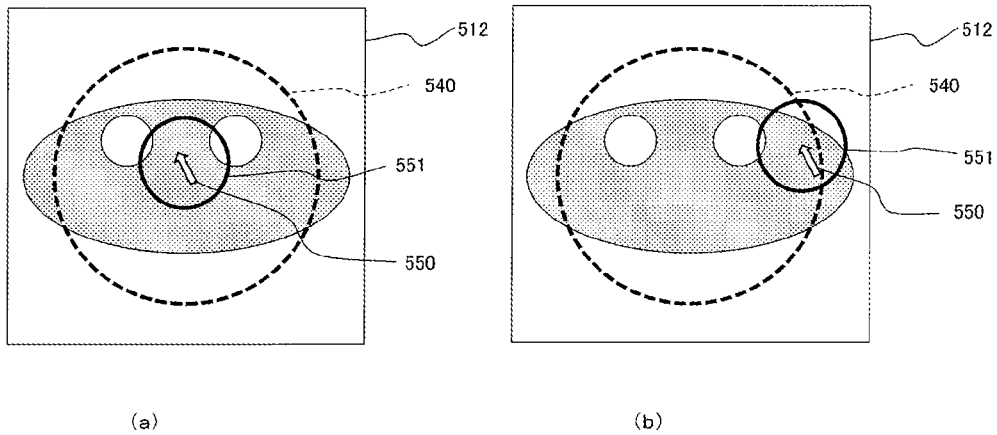
FIG. 11 is an explanatory drawing showing an example of display mode according to the second embodiment, wherein (a) indicates a case where a region including a specified point is within the circle in which the condition defined with the distance threshold $L_{th}$ is satisfied, (b) indicates a case where a region including a designated point is not within the circle in which the condition defined with the distance threshold $L_{th}$ is satisfied.

As already explained with reference to FIG. 2B, in the second embodiment, two of the same projection data are generated, all the missing data of one of the projection data are interpolated by the view direction interpolation processing to generate view direction interpolated projection data, and all the missing data of the other projection data are interpolated by the channel direction interpolation processing to generate channel direction interpolated projection data. Then, the reconstruction operation is performed with the view direction interpolated projection data to generate a view direction interpolated reconstructed image, and the reconstruction operation is also performed with the channel direction interpolated projection data to generate a channel direction interpolated reconstructed image. Then, a combined image is generated by combining the view direction interpolated reconstructed image and the channel direction interpolated reconstructed image, in which combined image, contribution ratios of the view direction interpolated reconstructed image and the channel direction interpolated reconstructed image differ depending on the position of pixel in the combined image. Hereafter, this embodiment will be explained with reference to FIGS. 8 to 11. FIG. 8 is a flowchart showing the flow of the processing according to the second embodiment. FIG. 9 includes explanatory drawings showing processing for combining reconstructed images. FIG. 10 includes explanatory drawings showing examples of display mode according to the second embodiment. FIG. 11 includes explanatory drawings showing examples of display mode according to the second embodiment, wherein (a) shows a case where a region including a specified point is within the region of the boundary marker indicating positions corresponding to the distance threshold $L_{th}$, and (b) shows a case where a region including a specified point is not within the region of the boundary marker indicating positions corresponding to the distance threshold $L_{th}$. FIG. 8 shows only the flow of the [image generation step] according to the second embodiment. The [imaging condition setting step] and the [imaging step] performed before the image generation step are as already described above, and therefore explanations thereof are omitted. Hereafter, explanations will be made for the steps shown in FIG. 8.

(Step S101)

First, a pre-processing required for the view direction interpolation processing and the channel direction interpolation processing is performed for the projection data (Step S101). As the pre-processing, specifically, correction of linearity of circuits, defect correction (defective pixel correction), and so forth are performed, for example. The linearity correction and defect correction are performed by using known technique.

(Steps S111 and S112)

Then, missing data occurring in connection with the FFS function are interpolated. One set (two) of projection data measured for the same slice position is prepared. The view direction interpolation processing is performed for one of the projection data at all the data missing positions on the projection data to generate view direction interpolated projection data (S111). For the other projection data, missing data at all the data missing positions on the projection data are interpolated by the channel direction interpolation processing to generate channel direction interpolated projection data (S112). The channel direction interpolation processing and view direction interpolation processing referred to above are the same as the processings explained for the first embodiment with reference to FIG. 6.

(Steps S103-1 and S103-2)

A pre-processing required for the log conversion or reconstruction processing is performed for the view direction interpolated projection data generated in Step S111 (Step S103-1). Similarly, a pre-processing required for the log conversion or reconstruction processing is performed also for the channel direction interpolated projection data generated in Step S112 (Step S103-2). These are also performed by using a known technique. The log conversion can also be performed in Step S101 performed before Steps S111 and S112.

(Steps S104-1 and S104-2)

A reconstruction operation is performed by using the view direction interpolated projection data to generate a reconstructed image (S104-1). Hereafter, this reconstructed image is referred to as "view direction interpolated reconstructed image" (corresponding to the reconstructed images 511 shown in FIG. 2B). Furthermore, a reconstruction operation is also performed by using the channel direction interpolated projection data to generate a reconstructed image (S104-2). This reconstructed image is henceforth referred to as "channel direction interpolated reconstructed image" (corresponding to the reconstructed images 512 shown in FIG. 2B). Therefore, two reconstructed images are generated in this step. As for the reconstruction algorithm, reconstruction may be performed by using, for example, the FeldKamp method or the sequential approximation method, which are known techniques, and type of the reconstruction algorithm is not particularly limited.

(Step S113)

Then, two reconstructed images generated in Steps S104-1 and S104-2 are combined (Step S113). Examples of the combination are shown in FIG. 9. In FIG. 9, the inside of the region enclosed with an ellipse is the subject region, and the circle 520 is the boundary of the first region 513a and the second region 513b. As for the example shown in FIG. 9(a), in the combined images 513, the view direction interpolated reconstructed image 511 is used for the first region 513a within the distance threshold $L_{th}$ (the circle 520 drawn with a solid line) from the reconstruction point 0 at the rotation center axis, the channel direction interpolated reconstructed image 512 is used for the second region 513b outside the first region, which includes positions of the distance threshold $L_{th}$, and they are combined to generate the combined image 513.

In the example shown in FIG. 9(b), there is provided a connection region 513c connecting the first region 513a and the second region 513b, which includes positions of the distance threshold $L_{th}$, in order to secure continuity in a region around the distance threshold $L_{th}$, and for this region 513c, the view direction interpolated reconstructed image 511 and the channel direction interpolated reconstructed image 512 are added. In FIG. 9(b), the connection region 513c is shown as a region between a broken line circle 531 concentric with the solid line circle 520 and having a radius shorter than the distance threshold $L_{th}$, and a broken line circle 532 concentric with the solid line circle 520 and having a radius longer than the distance threshold $L_{th}$. For addition of the view direction interpolated reconstructed image 511 and the channel direction interpolated reconstructed image 512, for example, only the view direction interpolated reconstructed image 511 is used for the first region 513a, and only the channel direction interpolated reconstructed image 512 is used for the second region 513b. Further, for the connection region 513c, a weighting factor (weight) determined according to the distance from the position of the distance threshold $L_{th}$ is multiplied on both the view direction interpolated reconstructed image 511 and the channel direction interpolated reconstructed image 512, and then they are added. The contribution ratios of the view direction interpolated reconstructed image and the channel direction interpolated reconstructed image can be thereby continuously changed in the connection region.

In FIG. 9, for example, a weighting factor that linearly changes according to change of the distance from the imaging center (reconstruction point at the rotation center) in the combined image 513 is used, and for a position of the distance threshold $L_{th}$, a weighting factor of 0.5 is multiplied on both the view direction interpolated reconstructed image 511 and the channel direction interpolated reconstructed image 512. As the position becomes closer to the imaging center O than the position of the distance threshold (position becomes closer to the first region 513a), the weight to be multiplied on the view direction interpolated reconstructed image 511 is made relatively larger than the weight to be multiplied on the channel direction interpolated reconstructed image 512. Further, as the position becomes remoter from the imaging center O than the position of the distance threshold (position closer to the second region 513b), the weight to be multiplied on the view direction interpolated reconstructed image 511 is made relatively smaller than the weight to be multiplied on the channel direction interpolated reconstructed image 512. Discontinuity at the combined position in the combined image 513 is thereby prevented, and therefore generation of artifacts at a position of the distance threshold $L_{th}$ can be reduced.

According to the first embodiment, when the reconstruction part calculates the distance threshold $L_{th}$, the boundary is determined as a point at which the resolution for the view direction and the resolution for the channel direction of the projection data become the same. However, the boundary may also be determined as a point at which the resolution for the view direction (angular direction) and the resolution for the channel direction become the same in the channel direction interpolated reconstructed image, or a point at which the resolution for the view direction (angular direction) and the resolution for the channel direction become the same in the view direction interpolated reconstructed image. In this case, as in the first embodiment, the determination may be performed by the reconstruction part using values calculated on the basis of the moving distance of the focal point of X-ray, or values calculated on the basis a resolution measurement image for measuring resolution corresponding to the distance from the rotation center.

(Step S114)

Finally, the image is displayed (Step S114). Candidates of the image to be displayed include the combined image 513, the channel direction interpolated reconstructed image 512, and the view direction interpolated reconstructed image 511, and one of these or arbitrary combination of these may be displayed. Diversified diagnosis is thereby enabled. As an example of the display mode, only the combined image 513 may be displayed as shown in FIG. 10. In this case, a boundary marker 540 that indicates the circle 520 corresponding to the distance threshold $L_{th}$ may be superimposingly displayed on the combined image 513. Change of the filter around the boundary marker 540 can be thereby informed to the operator. Further, the boundary marker 540 may not be displayed for legibility of the whole display.

As another example of the display mode, only the channel direction interpolated reconstructed image 512 may be displayed in an initial display, and the view direction interpolated reconstructed image 511 may be displayed in the inside thereof as required. The channel direction interpolated reconstructed image 512 shows higher uniformity of the resolution in the reconstructed image compared with the view direction interpolated reconstructed image 511. Therefore, the channel direction interpolated reconstructed image 512 may be displayed first so that the operator can see the whole image at a resolution that is uniform to a certain degree, and when the operator specifies a concerned position, the view direction interpolated reconstructed image 511 of a region including the specified position may be displayed instead. For example, as shown in FIG. 11(a), the boundary marker 540 corresponding to the distance threshold $L_{th}$ is superimposingly displayed on the channel direction interpolated reconstructed image 512 (in FIG. 11, it is displayed with a broken line). When an operation for specifying an arbitrary point within this boundary marker 540 is done (for example, moving a mouse cursor 550 to the specified position and clicking the mouse), a specified region 551 (drawn with a solid line in FIG. 11), of which center is the specified position, is set. For only the inside of this specified region 551, the view direction interpolated reconstructed image 511 showing higher resolution compared with the channel direction interpolated reconstructed image 512 is displayed instead of the latter. As shown in FIG. 11(b), if the specified region 551 of which center is the specified point protrudes out of the boundary marker 540 corresponding to the distance threshold $L_{th}$, for only the region within the boundary marker 540 of the specified region 551, the view direction interpolated reconstructed image 511 may be displayed instead of the channel direction interpolated reconstructed image 512. In this example of the display, if a region outside the boundary marker 540 is specified, substitution of the view direction interpolated reconstructed image 511 is not performed. In addition, in the example of the display shown in FIG. 11, a processing for calculating the distance threshold is performed in Step S113, and the combining processing is unnecessary.

According to this embodiment, the difference of the view number of the samplings and the channel number of the samplings occurring depending on the imaging position in the reconstructed image can be reduced. Further, since a plurality of interpolated images (view direction interpolated reconstructed image, channel direction interpolated reconstructed image, and combined image) are generated, an interpolated image of a resolution desired by a user can be displayed, and thus there can be expected an effect that diversified diagnosis can be more easily performed.

As a modification of the second embodiment, there may be used a filter function that continuously changes the weighting factor to be multiplied on the view direction interpolated reconstructed image and the weighting factor to be multiplied on the channel direction interpolated reconstructed image used in the combined image 513 according to the distance from the imaging center. The difference of the view number of the samplings and the channel number of the samplings can be thereby continuously reduced for the whole connection region. As an example of this filter function, a trigonometric function of which value changes according to the distance from the rotation center of the rotational movement (imaging center in the combined image) may be used.

Third Embodiment

Figure 12:
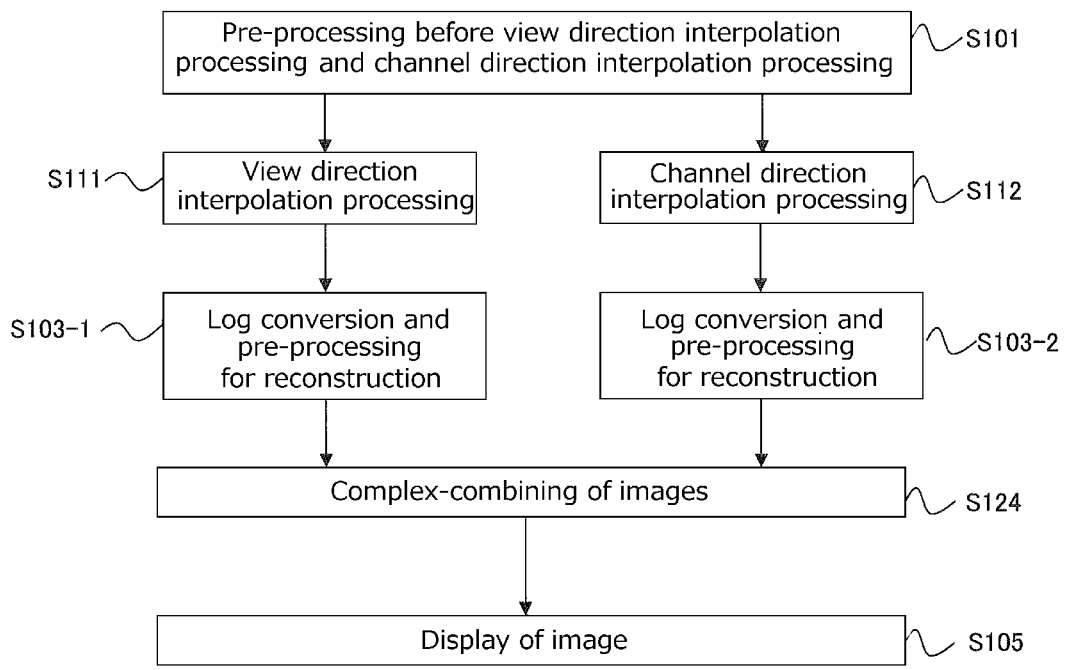
FIG. 12 is a flowchart showing the flow of the processing according to the third embodiment.

According to the second embodiment, in order to generate the view direction interpolated reconstructed image and the channel direction interpolated reconstructed image, it is necessary to perform the reconstruction operation processing twice. Therefore, the reconstruction operation time is doubled. Accordingly, according to the third embodiment, by changing the projection data used according to the pixel position during the reconstruction operation, the reconstruction operation is finished at once to shorten the reconstruction operation time. Since the [imaging condition setting step] and the [imaging step] used in the third embodiment are also the same as those of the first embodiment, explanations thereof are omitted, and only the [image generation step] will be explained below. Hereafter, the third embodiment will be explained with reference to FIG. 2(c) and FIG. 12. FIG. 12 is a flowchart showing the flow of the processing of the image generation step according to the third embodiment. Hereafter, the third embodiment will be explained in the order of the steps shown in FIG. 12, but for the processings common to the first and second embodiments, only the outlines are described, and detailed explanations are omitted.

(Steps S101, S111, S112, S103-1 and S103-2)

As in the second embodiment, one set (two) of the same projection data is prepared, and a pre-processing required for the view direction interpolation processing and the channel direction interpolation processing is performed for each of them (S101). Subsequently, the view direction interpolation processing (S111) and the channel direction interpolation processing (S112) are performed for them, respectively. Then, a pre-processing for the log conversion or reconstruction processing is performed for the projection data having been subjected to the interpolation processings in Steps S111 and S112 (S103-1, S103-2).

(Step S124)

Then, complex reconstruction is performed (Step S124). The "complex reconstruction" referred to here means generating one reconstructed image by performing a reconstruction operation using a plurality of kinds of projection data. Ratio of use of the projection data used for the reconstruction processing is thereby changed according to the position of the pixel in the reconstructed image to optimize the interpolation levels for the view direction and the channel direction, and thereby improve the spatial resolution of the reconstructed image.

A specific reconstruction procedure will be explained. The convolution method, which is a known technique, is first used. This is a method of weighting the projection data to be used for calculating pixel values of pixels of a reconstructed image according to the positions of the pixels in the reconstructed image (position of the pixels in the real space), and adding them. That is, since to which pixel on the reconstructed image each pixel value corresponds can be known at the time of the addition, ratios of the view direction interpolated projection data (501A in FIG. 2C) and the channel direction interpolated projection data (502A in FIG. 2C) used for the optimal projection data for that pixel are determined, and then the convolution operation is performed with them.

For example, in the reconstructed image 515 shown in FIG. 2(c), for missing data in the first region inside the circle 520, which indicates positions at the distance threshold $L_{th}$ from the imaging center (the imaging center is regarded to be the same as the reconstruction point at the rotation center in this embodiment), the reconstruction operation is performed by the convolution method using weight of 0 for the channel direction interpolated projection data 502A and weight of 1 for the view direction interpolated projection data 501A. That is, in the first region inside the circle 520, the reconstruction operation is performed by using only the view direction interpolated projection data 501A. For missing data of the second region outside the circle 520, but including positions on the circle 520, the reconstruction operation is performed by the convolution method using weight of 0 for the view direction interpolated projection data 501A and weight of 1 for the channel direction interpolated projection data 502A. That is, for this region, the reconstruction operation is performed by using only the channel direction interpolated projection data 502A. In addition, when the reconstruction part calculates the distance threshold $L_{th}$, a point where resolution for the view direction (angular direction) and resolution for the channel direction become the same in the channel direction interpolated reconstructed image, or a point where resolution for the view direction (angular direction) and resolution for the channel direction become the same in the view direction interpolated reconstructed image may be determined as the boundary. In this case, as in the first embodiment, the reconstruction part may calculate it by using values calculated on the basis of the moving distance of the focal point of X-ray, or values calculated on the basis of a resolution measurement image for determining resolution corresponding to the distance from the rotation center. Although this embodiment has been explained by exemplifying the convolution method as the algorithm of the reconstruction operation processing, it is not limited to the convolution method so long as an algorithm with which the coordinates of the imaging position in the real space or the real coordinates in the reconstructed image of the same can be clarified is used.

(Step S105)

As in the first embodiment, the generated reconstructed image is displayed (S105). Alternatively, as shown in FIG. 11 referred to in the explanation of the second embodiment, the channel direction interpolated reconstructed image may be displayed in an initial display, the boundary marker 540 that indicates the circle 520 corresponding to the distance threshold $L_{th}$ may be superimposingly displayed thereon, and when a specified region is set in the inside of the boundary marker 540, there may be displayed a reconstructed image generated by performing the reconstruction operation by the convolution method with the projection data using the first weight and second weight determined according to the imaging position in the specified region (position in the reconstructed image 515).

According to this embodiment, a reconstructed image in which the difference of the view number of the samplings and the channel number of the samplings in the reconstructed image is reduced can be generated by performing the reconstruction operation only once. Therefore, it has an advantage that amount of memory eventually required can be made smaller compared with the second embodiment.

As a modification of this embodiment, as in the second embodiment, in order to prevent formation of a discontinuous region at the circle 520 in the reconstructed images 515, a connection region that includes the circle 520 and connects the first region and the second region may be provided, and the convolution operation may be performed for the missing data in the connection region by using a relatively larger first weight factor to be multiplied on the view direction interpolated projection data 501A for a position closer to the imaging center and a relatively larger second weight factor to be multiplied on the channel direction interpolated projection data 502A for a position remoter from the imaging center in the connection region, so that the first weight and the second weight are continuously changed.

There may also be used a filter function that continuously changes the first weighting factor to be multiplied on the view direction interpolated projection data 501A and the second weighting factor to be multiplied on the channel direction interpolated projection data 502A according to the distance from the imaging center in the reconstructed image 515. The difference of the view number of the samplings and the channel number of the samplings can be thereby continuously reduced for the whole reconstructed image. As an example of this filter function, a trigonometric function of which value changes according to the distance from the rotation center of the rotational movement (imaging center in the reconstructed image 515).

DESCRIPTION OF NUMERICAL NOTATIONS

100 . . . X-Ray CT device
110 . . . Subject
200 . . . Input part
210 . . . Imaging condition input part
211 . . . Keyboard
212 . . . Mouse
213 . . . Monitor
300 . . . Imaging part
310 . . . X-Ray generation part
311 . . . X-Ray tube
313, 313a, and 313b . . . X-Ray focal point
320 . . . X-Ray detection part
321 . . . X-ray detection module
330 . . . Gantry
331 . . . Bore
332 . . . Rotation plate
340 . . . Imaging control part
341 . . . X-Ray controller
342 . . . Gantry controller
343 . . . Table controller
344 . . . Detection device controller
345 . . . Master controller
350 . . . Table for placing subject
400 . . . Image generation part
410 . . . Signal collection part
411 . . . Data acquisition system (DAS)
420 . . . Data processing part
421 . . . Central processing unit
422 . . . Memory
423 . . . HDD device
430 . . . Image display part
431 . . . Image display monitor

The invention claimed is:

1. An X-ray CT device comprising:
    an X-ray generation part that generates an X-ray,
    an X-ray detection part that has a plurality of X-ray detectors for detecting the X-ray, detects a transmitted X-ray, and outputs projection data,
    a rotation part that oppositely disposes the X-ray generation part and the X-ray detection part, and rotationally moves the X-ray generation part and the X-ray detection part,
    a projection data interpolation part that interpolates the projection data,
    a reconstruction part that performs a reconstruction operation using the interpolated projection data, and generates a reconstructed image, and
    a focal point moving part that moves a focal point of the X-ray alternately to a plurality of positions on a rotation orbit plane of the rotational movement, wherein:
    the X-ray detection part is constituted with the plurality of X-ray detectors arranged in the channel direction along the rotational direction,
    the projection data includes missing of data occurring in connection with movement of the focal point,
    the projection data interpolation part interpolates data at data missing positions of the projection data, with a view direction interpolation processing for interpolating the data using real data of the projection data lining up along the angular direction of the rotational movement and a channel direction interpolation processing for interpolating the data using real data of the projection data lining up along the channel direction, and
    the reconstruction part generates a reconstructed image in which contribution ratios of the projection data having been subjected to the view direction interpolation processing and the projection data having been subjected to the channel direction interpolation processing are different depending on position of pixel in the reconstructed image.

2. The X-ray CT device according to claim 1, wherein:
    the projection data interpolation part changes ratios of the view direction interpolation processing and channel direction interpolation processing to be performed according to the data missing position.

3. The X-ray CT device according to claim 1, wherein:
    the projection data interpolation part divides the projection data into a plurality of regions according to distance from the rotation center of the rotational movement, interpolates the data of the data missing positions in a first region relatively closer to the rotation center with the view direction interpolation processing, and interpolates the data of the data missing positions in a second region relatively remoter from the rotation center with the channel direction interpolation processing.

4. The X-ray CT device according to claim 3, wherein: the projection data interpolation part divides the projection data into the first region and the second region with a boundary indicating a position at which spatial resolution for the angular direction and spatial resolution for the channel direction of the projection data become the same.

5. The X-ray CT device according to claim 4, wherein: the projection data interpolation part provides a connection region including a part of the first region and a part of the second region around the boundary, and continuously changes ratios of the view direction interpolation processing and channel direction interpolation processing to be performed in the connection region.

6. The X-ray CT device according to claim 4, wherein: the projection data interpolation part determines the boundary using a value calculated on the basis of moving distance of the focal point of the X-ray, or a value calculated on the basis of a resolution measurement image for determining resolution according to the distance from the rotation center.

7. The X-ray CT device according to claim 1, wherein: the projection data interpolation part generates two of the same projection data, interpolates data of the data missing positions of one of the projection data with the view direction interpolation processing to generate view direction interpolated projection data, and interpolates data of the data missing positions of the other projection data with the channel direction interpolation processing to generate channel direction interpolated projection data, and the reconstruction part generates the reconstructed image by using the view direction interpolated projection data, and the channel direction interpolated projection data.

8. The X-ray CT device according to claim 7, wherein: the reconstruction part performs a reconstruction operation with the view direction interpolated projection data to generate a view direction interpolated reconstructed image, performs a reconstruction operation with the channel direction interpolated projection data to generate a channel direction interpolated reconstructed image, and generates a combined image by combining the view direction interpolated reconstructed image and the channel direction interpolated reconstructed image, in which contribution ratios of the view direction interpolated reconstructed image and the channel direction interpolated reconstructed image differ according to position of pixel in the combined image.

9. The X-ray CT device according to claim 8, wherein: the reconstruction part generates the combined image by providing a plurality of regions divided according to the distance from a reconstruction point of the rotation center and using the view direction interpolated reconstructed image for a first region relatively closer to the reconstruction point of the rotation center and the channel direction interpolated reconstructed image for a second region relatively remoter from the reconstruction point of the rotation center, so that the combined image is generated as an image generated by combining the view direction interpolated reconstructed image of the first region and the channel direction interpolated reconstructed image of the second region.

10. The X-ray CT device according to claim 9, wherein: the X-ray CT device further comprises an operation part for specifying an arbitrary point on the channel direction interpolated reconstructed image, and the reconstruction part superimposingly displays a boundary marker that indicates the boundary of the first region and the second region on the channel direction interpolated reconstructed image, and replaces the channel direction interpolated reconstructed image within a specified region including the point specified by an operator through the operation part in the first region of the channel direction interpolated reconstructed image by the view direction interpolated reconstructed image.

11. The X-ray CT device according to claim 9, wherein: the reconstruction part divides the combined image into the first region and the second region with a boundary that indicates a point at which spatial resolution for the angular direction and spatial resolution for the channel direction of the channel direction interpolated reconstructed image become the same, or a point at which spatial resolution for the angular direction and spatial resolution for the channel direction of the view direction interpolated reconstructed image become the same.

12. The X-ray CT device according to claim 11, wherein: the reconstruction part provides a connection region including a part of the first region and a part of the second region around the boundary, and continuously changes contribution ratios of the view direction interpolated reconstructed image and the channel direction interpolated reconstructed image in the connection region.

13. The X-ray CT device according to claim 7, wherein: the reconstruction part generates the reconstructed image by performing a convolution operation for the interpolated projection data with making first weighting factor to be multiplied on the view direction interpolated projection data relatively larger than second weighting factor to be multiplied on the channel direction interpolated projection data for a position relatively closer to the reconstruction point of the rotation center in the reconstructed image, and making the second weighting factor relatively larger than the first weighting factor for a position relatively remoter from the reconstruction point of the rotation center in the reconstructed image.

14. The X-ray CT device according to claim 13, wherein: the reconstruction part sets a plurality of sections divided according to the distance from the reconstruction point of the rotation center in the reconstructed image, and performs the convolution operation with a value of 1 as the first weighting factor and a value of 0 as the second weighting factor for the first region relatively closer to the reconstruction point of the rotation center, and a value of 0 as the first weighting factor and a value of 1 as the second weighting factor for the second region relatively remoter from the reconstruction point of the rotation center.

15. The X-ray CT device according to claim 14, wherein: the reconstruction part divides the reconstructed image into the first region and the second region with a boundary indicating a point at which resolution for the angular direction and resolution for the channel direction of the projection data measured with moving the focal point of the X-ray become the same.

16. The X-ray CT device according to claim 15, wherein: the reconstruction part provides a connection region including a part of the first region and a part of the second region around the boundary, and continuously changes the first weighting factor and the second weighting factor in the connection region.

17. The X-ray CT device according to claim 11, wherein: the reconstruction part determines the boundary using a value calculated on the basis of moving distance of the focal point of the X-ray, or a value calculated on the basis of a resolution measurement image for determining resolution according to the distance from the rotation center.

18. The X-ray CT device according to claim 1, wherein: the reconstruction part generates the reconstructed images using a filter function that continuously changes contribution ratios of the projection data having been subjected to the view direction interpolation processing and the projection data having been subjected to the channel direction interpolation processing according to the distance from the rotation center of the rotational movement.

19. The X-ray CT device according to claim 18, wherein: the filter function is a trigonometric function of which value changes according to the distance from the rotation center of the rotational movement.

20. A method for reconstructing an image using projection data obtained by performing imaging with an X-ray CT device comprising an X-ray generation part that generates an X-ray, an X-ray detection part that has a plurality of X-ray detectors for detecting the X-ray, detects a transmitted X-ray, and outputs projection data, a rotation part that oppositely disposes the X-ray generation part and the X-ray detection part, and rotationally moves the X-ray generation part and the X-ray detection part, and a focal point moving part that moves a focal point of the X-ray alternately to a plurality of positions on a rotation orbit plane of the rotational movement, in which the X-ray detection part is constituted with the plurality of X-ray detectors arranged in the channel direction along the rotational direction, and the rotational movement is performed with moving the focal point of the X-ray alternately to the positions, wherein the projection data includes missing of data associated with the movement of the focal point, and the method comprises:

interpolating data of data missing positions, with a view direction interpolation processing for interpolating the data using real data of the projection data lining up along the angular direction of the rotational movement and a channel direction interpolation processing for interpolating the data using real data of the projection data lining up along the channel direction, and generating a reconstructed image in which contribution ratios of the projection data having been subjected to the view direction interpolation processing and the projection data having been subjected to the channel direction interpolation processing are different depending on position of pixel in the reconstructed image.

* * * * *